US006530234B1

(12) United States Patent
Dobak, III et al.

(10) Patent No.: US 6,530,234 B1
(45) Date of Patent: Mar. 11, 2003

(54) PRECOOLING SYSTEM FOR JOULE-THOMSON PROBE

(75) Inventors: John D. Dobak, III, Del Mar; Terry L. Brown, San Diego; Kambiz Ghaerzadeh, San Jose; Xiaoyu Yu, San Diego, all of CA (US)

(73) Assignee: CryoGen, Inc., San Diego, CA (US)

( * ) Notice: Subject to any disclaimer, the term of this patent is extended or adjusted under 35 U.S.C. 154(b) by 368 days.

(21) Appl. No.: 09/075,374

(22) Filed: May 7, 1998

Related U.S. Application Data (63) Continuation-in-part of application No. 08/726,770, filed on Oct. 7, 1996, now Pat. No. 5,758,505, which is a continuation-in-part of application No. 08/698,044, filed on Aug. 15, 1996, now Pat. No. 5,787,715, which is a continuation-in-part of application No. 08/542,123, filed on Oct. 12, 1995.
(60) Provisional application No. 60/054,168, filed on Jul. 30, 1997.

(51) Int. Cl.[7] .................................................. F17C 7/02
(52) U.S. Cl. ............................................................ 62/52.1
(58) Field of Search .................................. 62/51.2; 606/20

(56) References Cited

U.S. PATENT DOCUMENTS

| | | | |
|---|---|---|---|
| 2,319,542 A | 5/1943 | Hall | 128/400 |
| 2,672,032 A | 3/1954 | Towse | 62/126 |
| 2,991,633 A | * 7/1961 | Simon | 62/51.2 |
| 3,048,021 A | * 8/1962 | Coles et al. | 62/51.2 |
| 3,272,203 A | 9/1966 | Chato | 128/303.1 |
| 3,273,356 A | 9/1966 | Hoffman | 62/51.2 |
| 3,298,371 A | 1/1967 | Lee | 62/293 |
| 3,369,549 A | 2/1968 | Armao | |
| 3,398,738 A | 8/1968 | Lamb et al. | 128/303.1 |
| 3,401,533 A | 9/1968 | Maybury | 62/51.2 |
| 3,415,078 A | * 12/1968 | Liston | 62/51.2 |
| 3,431,750 A | 3/1969 | Lefranc | 62/51.2 |

(List continued on next page.)

FOREIGN PATENT DOCUMENTS

| | | |
|---|---|---|
| EP | 0271989 | 6/1988 |
| FR | 1465540 | 1/1967 |
| FR | 1468862 | 1/1967 |
| FR | 2 482 445 | 3/1980 |
| FR | 2 477 406 | 9/1981 |
| FR | 2477406 | 9/1981 |

(List continued on next page.)

OTHER PUBLICATIONS

Chang, Zhaohua; Development of a High-Performance Multiprobe Cryosurgical Device; pp. 383–390; Sep., 1994; Biomedical Instrumentation and Technology, vol. 28.
Coxeter, Ruth; Developments to Watch—_The Deep Freeze for Irregular Heartbeats; p. 90; Sep. 19, 1994; Business Week.
Friend, Daniel G.; Thermophysical Property Computer Packages from NIST; pp. 13–18; 1992; ASME HTD vol. 225, Computerized Thermophysical Property Packages.

(List continued on next page.)

*Primary Examiner*—Ronald Capossela
(74) *Attorney, Agent, or Firm*—Gerald W. Spinks (57) ABSTRACT

A miniature refrigeration system and method of operation. A primary refrigerant is pressurized by a compressor to a relatively low pressure, for safety reasons. The compressed primary refrigerant is passed through a primary-to-secondary heat exchanger, to precool the gas mixture. The secondary side of the primary-to-secondary heat exchanger is cooled by a secondary refrigeration system. The primary refrigerant exiting the primary outlet of the primary-to-secondary heat exchanger passes to a primary Joule-Thomson expansion element where the high pressure gas is expanded to a lower temperature. This low temperature gas cools a heat transfer element mounted in the outer wall of the catheter or cryoprobe, to cool surrounding tissue. Return gas can flow back through a distal primary-to-primary heat exchanger to further cool the incoming high pressure gas mixture. A proximal primary-to-primary heat exchanger can be added between the primary-to-secondary heat exchanger and the primary compressor.

21 Claims, 5 Drawing Sheets

U.S. PATENT DOCUMENTS

| | | | |
|---|---|---|---|
| 3,439,680 A | 4/1969 | Thomas, Jr. | 128/303.1 |
| 3,477,434 A | 11/1969 | Hood, Jr. et al. | 128/303.1 |
| 3,536,075 A | 10/1970 | Thomas, Jr. | 128/303.1 |
| 3,613,689 A | 9/1971 | Crump et al. | 128/303.1 |
| 3,630,203 A | 12/1971 | Sellinger et al. | 128/303.1 |
| 3,662,755 A | 5/1972 | Rautenbach et al. | 128/303.1 |
| 3,696,813 A * | 10/1972 | Wallach | 62/51.2 X |
| 3,729,945 A | 5/1973 | Linnett | 62/40 |
| 3,750,417 A | 8/1973 | Johannes et al. | 62/114 |
| 3,768,273 A | 10/1973 | Missimer | 62/84 |
| 3,786,814 A | 1/1974 | Armao | |
| 3,827,436 A | 8/1974 | Stumpf et al. | |
| 3,889,680 A | 6/1975 | Armao | 128/303.1 |
| 3,913,581 A | 10/1975 | Ritson et al. | 128/303.1 |
| 3,924,628 A | 12/1975 | Droegemueller et al. | 128/303.1 |
| 3,932,154 A | 1/1976 | Coers et al. | 62/9 |
| 3,971,383 A | 7/1976 | Kishi | |
| 4,015,606 A | 4/1977 | Mitchiner et al. | 62/293 |
| 4,206,609 A | 6/1980 | Durenec | 62/6 |
| 4,207,897 A | 6/1980 | Lloyd et al. | 128/303.1 |
| 4,211,231 A | 7/1980 | Rzasa | 128/303.1 |
| 4,275,734 A | 6/1981 | Mitchiner | 128/303.1 |
| 4,377,168 A | 3/1983 | Rzasa et al. | 128/303.1 |
| 4,601,296 A | 7/1986 | Yerushaimi | |
| 4,781,033 A | 11/1988 | Steyert et al. | 62/51.2 |
| 4,829,785 A | 5/1989 | Hersey | 62/51.2 X |
| 4,840,043 A | 6/1989 | Sakitani et al. | 62/51.2 |
| 4,875,346 A | 10/1989 | Jones et al. | 62/467 |
| 4,951,471 A | 8/1990 | Sakitani et al. | 62/51.2 |
| 4,990,412 A | 2/1991 | Hersey | 429/8 |
| 5,063,747 A | 11/1991 | Jones et al. | 62/461 |
| 5,077,979 A | 1/1992 | Skertic et al. | 62/51.2 |
| 5,078,713 A | 1/1992 | Varney | 606/23 |
| 5,101,894 A | 4/1992 | Hendricks | 62/51.2 |
| 5,139,496 A | 8/1992 | Hed | 606/23 |
| 5,147,355 A | 9/1992 | Friedman et al. | 606/23 |
| 5,150,579 A | 9/1992 | Hingst | 62/51.2 |
| 5,157,938 A | 10/1992 | Bard et al. | 62/335 |
| 5,193,349 A | 3/1993 | Laverman et al. | 62/64 |
| 5,275,595 A | 1/1994 | Dobak, III | 606/23 |
| 5,281,212 A | 1/1994 | Savage et al. | 606/15 |
| 5,281,213 A | 1/1994 | Milder et al. | 606/15 |
| 5,281,215 A | 1/1994 | Milder | 606/20 |
| 5,281,217 A | 1/1994 | Edwards et al. | 606/41 |
| 5,324,286 A | 6/1994 | Fowle | 606/23 |
| 5,334,181 A | 8/1994 | Rubinsky et al. | 606/22 |
| 5,337,572 A | 8/1994 | Longsworth | 62/51.2 |
| 5,365,750 A | 11/1994 | Greenthal | 62/51.2 |
| 5,403,309 A | 4/1995 | Coleman et al. | 606/20 |
| 5,423,807 A | 6/1995 | Milder | 606/20 |
| 5,476,090 A | 12/1995 | Kishi | |
| 5,522,870 A | 6/1996 | Ben-Zion | 607/104 |
| 5,573,532 A | 11/1996 | Chang et al. | 606/26 |
| 5,595,065 A | 1/1997 | Boiarski et al. | 62/51.2 X |
| 5,617,739 A * | 4/1997 | Little | 62/114 X |
| 5,644,502 A | 7/1997 | Little | 364/496 |
| 5,674,218 A | 10/1997 | Rubinsky et al. | 606/20 |
| 5,724,832 A | 3/1998 | Little et al. | 62/613 |
| 5,807,391 A | 9/1998 | Wijkamp | 606/23 |

FOREIGN PATENT DOCUMENTS

| | | |
|---|---|---|
| GB | 1 336 892 | 11/1973 |
| GB | 2 026 324 | 2/1980 |
| GB | 2 080 117 | 2/1982 |
| GB | 2 093 964 | 9/1982 |
| GB | 2 289 413 | 1/1995 |
| GB | 2 283 678 | 5/1995 |
| GB | 2 289 412 | 11/1995 |
| GB | 2 289 414 | 11/1995 |
| GB | 2 289 510 | 11/1995 |
| JP | 57-126430 | 8/1982 |
| SU | 333857 | 4/1974 |
| SU | 333858 | 4/1974 |
| SU | 527467 | 9/1976 |
| SU | 534484 | 11/1976 |
| SU | 565052 | 7/1977 |
| SU | 573496 | 9/1977 |
| SU | 627154 | 8/1978 |
| SU | 637417 | 12/1978 |
| SU | 676604 | 7/1979 |
| SU | 768795 | 10/1980 |
| SU | 802348 | 2/1981 |
| SU | 802349 | 2/1981 |
| SU | 802350 | 2/1981 |
| SU | 802351 | 2/1981 |
| SU | 832268 | 5/1981 |
| SU | 839516 | 6/1981 |
| SU | 0 839 516 | 6/1981 |
| SU | 918298 | 4/1982 |
| SU | 966107 | 10/1982 |
| SU | 1054400 | 1/1983 |
| SU | 1026795 | 7/1983 |
| SU | 1026796 | 7/1983 |
| SU | 1089099 | 4/1984 |
| SU | 1090699 | 5/1984 |
| SU | 1134856 | 1/1985 |
| SU | 1158567 | 5/1985 |
| SU | 1189434 | 11/1985 |
| SU | 1437012 | 11/1988 |
| SU | 1774140 | 11/1992 |
| SU | 1 774 140 | 11/1992 |
| WO | WO 93/04647 | 3/1993 |
| WO | WO 93/08753 | 5/1993 |
| WO | WO95/13025 | 1/1994 |
| WO | WO 95/30379 | 11/1995 |
| WO | Wo 95/30380 | 11/1995 |

OTHER PUBLICATIONS

Gage, Andrew A.; Current Progress in Cryosurgery; pp. 483–486; Mar. 28, 1988; American College of Cryosurgery, 8th Annual Meeting.

Hill, Dennis; *Throttle Cycle Cooler Vibration Characterization*; 5 pages; date and place of publication unknown.

Hubbell, Richard H.; New Heat Transfer and Friction Design Data for Perforated Plate Heat Exchangers; pp. 383–390; 1988; Advanced Cryogenic Engineering, vol. 33.

Jichuan, Hu; Heat Transfer Characteristics of a Perforated Plate: Part II—Heat Transfer Coefficients for the Separate Working Surfaces; pp. 318–322; Sep., 1990; Cryogenics, vol. 30.

Jones, Jack A.; *Cryogenic Mixed Fluid Application Study and Computer Code Development, Final Report*; pp. i–18; date and place of publication unknown.

Kratri, Ajay; *A Throttle Cycle Cryocooler Operating with Mixed Gas Refrigerants in 70K to 120K Temperature Range*; 5 pages; dates and place of publication unknown.

Khatri, Ajay; *A Throttle Cycle Refrigerator Operating Below 77K*; 8 pages; date and place of publication unknown.

Little, W. A.; *Advances in Joule–Thomson Cooling*; pp. 1–10; date and place of publication unknown.

Little, W. A.; Microminiature Refrigeration; pp. 661–680; May, 1984; Rev. Sci. Instrum. vol. 55 (5).

Little, W. A.; Microminiature Refrigerators for Joule–Thomson Cooling of Electronic Chips and Devices; pp. 1325–1333; 1990; Advances in Cryogenic Engineering, vol. 35.

Venkatarathnam, G.; Heat Transfer and Flow Friction Correlations in Perforated Plate Matrix Heat Exchangers; pp. 313–317; Sep., 1990; Cryogenics, vol. 30.

Venkatarathnam, G.; Matrix Heat Exchangers and Their Application in Cryogenic Systems; pp. 907–918; Nov., 1990; Cryogenics, vol. 30.

Abstract 907,054; A. V. Mostitskiy.

S. Bard, *A Two–Stage 80 K/140 K Sprption Cryocooler*, Proceedinngs of the 12th International Cryogenic Engineering Conference, pp. 626–630. (R.G. Scurlock and C.A. Bailey, eds.) Butterworth, Guilford, UK 1988);.

J. Baust; *Underlying Mechanism of Damage and New Concepts in Bryosurgery*, Cryosurgery: Mechanisms and Applications, pp. 21–36 (International Institute of Refrigeration, Paris 1995).

E. Bodio, *The application of Multicomponent Gaseous Mixtures in Linde–Hampson Coolers*, Wroclaw Institute of Tech. (1985); Partial translation to English.

V. M. Brojanski; *Developments in Cryotechnology to 2000*; May 1989; pp. 193–195; 16th Cryotechnology Congress; Translated to English.

Z. Chang; *Optimization of Cryosurgical Instrumentation for Use in Minimally Invasive Prostrate Surgery*; 1993; pp. 45–55; Recent Advances in Cryogenic Engineering.

W. Bald; *Cryogenic Surgery*; pp. 1383–1434, Reports on Progress in Physics; date unknown.

W. Droegemueller; *Cryocoagulation of the Endometrium at the Uterine Cornua*; May 1978; pp. A58–A66; American Journal of Obstetrics and Gynecology.

A. Gage; *Cryosurgery*; date unknown; pp. 893–908; Encyclopedia of Medical Devices and Instrumentation.

G. Garamy; *Engineering Aspects of Cryosurgical Instruments Employing Liquid Nitrogen*; 1967; pp. 283–308; International Ophthalmology Clinics.

J. Jones; *Mixed Gas Sorption Joule–Thomson Refrigerator*; May 1991; pp. i, 1–4; NASA Tech Brief.

J. Jones; *Sorption Refrigeration Research at JPL/NASA*; 1992; pp. 143–152; International Institute of Refrigeration.

Author unknown; *Technical Support Package on Mixed Gas Sorption Joule–Thomson Refrigerator*; May 1991; Jet Propulsion Lab.

A. Kleemenko; *One Flow Cascade Cycle(In Schemes of Natural Gas Liquefaction and Separation)*; 1959; pp. 34–39; Proceedings of International Congress of Refrigeration.

V. Kobryanskiy; *A Cryomedical Device Based on a Closed Cycle Joule–Thomson Cooling System*; Mar. 1978; pp. 71–72; place of publication unknown –Translated to English.

W. Little; *Development of a Low Cost, Cryogenic Refrigeration System for Cooling of Cryoelectronics*; 1994; pp. 1467–1474; Advances in Cryogenic Engineering, vol. 39.

W. Little; *Microminiature Refrigerators for Joule–Thomson Cooling of Electronic Chips and Devices*; 1990; pp. 1325–1333; Advances in Cryogenic Engineering, vol. 35.

W. Little; *Recent Developments in Joule–Thomson Cooling: Gases, Coolers and Compressors*; 9 pages; date and place of publication unknown.

W. Porter; *Processor Performance Enhancement Using CPU Sub–Cooling*; 1994; pp. 242–246; Proceedings of the International Electronic Packaging Conference.

Y. Rabin; *A Compact Cryosurgical Apparatus for Minimally Invasive Procedures*; May 1997; pp. 251–258; Biomedical Instrumentation and Technology.

S. Sood; *Prediction Methods for Vapor–Liquid Equilibria in Multi–Component Cryogenic Mixtures*; Jun. 1970; pp. 199–207; Cryogenics.

D. Torre; *Alternate Cryogens for Cryosurgery*; Jun. 1975; pp. 56–58; Journal Of Dermatologic Surgery.

A. Gassanov; *Experience with the Development and Use of Cryogenic Surgical Equipment*; Sep. 1986; pp. 41–42; place of publication unknown –Translated to English.

A. Grokholski; *The Krioelektronika–1 Cryogenic Dental Unit*; Sep. 1981; pp. 16–20; Meditsinskaya Teknika –Translated to English.

Addonizio, J.C., *Another Look at Cryoprostatectomy*, 19 Cryobiology 223–227, 1982.

Little, W.A. Handwritten Notes to Valley Laboratories, Bates Nos. M00001–M00009, Apr. 1987.

*Military & Commericial Applications for Low Cost Cryocoolers*, Electronic Industries Association Cryoelectronics Division, Jan. 31 and Feb. 1, 1996.

The "Cheetah" System, a cooling system manufactured and sold by Defendant MMR Technologies, Inc.

File History of U.S. Patent No. 5,910,104.

Cryogen Documents, Bates, No. CRY 000428–CRY 000479.

Answer, Affirmative Defenses, and Counterclaims of Defendant Johnson & Johnson to CryoGen's First Amended Complaint for Infringement of U.S. Patent Nos. 5,758,505 & 5,910,104, *CryoGen, Inc. v. Johnson & Johnson, Inc.*, Case No. C–99–02471 VRW (N. D. Cal. Aug. 31, 1999).

Answer, Affirmative Defenses, and Counterclaims of Defendants FemRx and Ethicon to CryoGen's First Amended Complaint for Infringement of U.S. Patent Nos. 5,758,505 & 5,910,104, *CryoGen, Inc. v. Johnson & Johnson, Inc.*,Case No. C–99–02471 VRW, (N.D. Cal. Jul. 1, 1999).

Answer, Affirmative Defenses, and Counterclaims of Defendants MMR Technologeis, Inc. to First Amended Complaint for Infringement of U.S. Patent Nos. 5,758,505 & 5,910,104, *CryoGen, Inc. v. Johnson & Johnson, Inc.*, Case No. C–99–02471 VRW (N.D. Cal. Jul. 1 1999).

Supplemental Responses and Objections of FemRx, Inc., Ethicon, Inc., and Johnson to CryoGen, Inc. 's Second Set of Interrogatories, *CryoGen, Inc. v. Johnson & Johnson, Inc.*, Case No. C–99–02471 VRW (N.D. Cal. Jul. 1, 1999), Case No. C–99–02474 VRW (N.D. Cal. Jan. 4–7.

Deposition of Gerald W. Spinks, Esq. of Spinks ("Spinks Dep."): 57–147, 148–233, 246–275, 275–325 (submitting under M.P.E.P. § 724.02).

Docket Sheet, *CryoGen, Inc. v. Johnson & Johnson, Inc.*, Case No. C99–02471 VRW (N.D. Cal. filed May 25, 1999) (updated Mar. 30, 2000).

Docket Sheet, *FemRx, Inc. v. CryoGen, Inc.*, Case No. C98–02330 VRW (N.D. Cal. filed Jun. 8, 1998) (updated Mar. 30, 2000).

\* cited by examiner

PRECOOLING SYSTEM FOR JOULE-THOMSON PROBE

CROSS REFERENCE TO RELATED APPLICATIONS

This application is a continuation-in-part of prior copending U.S. patent application Ser. No. 08/726,770, filed Oct. 7, 1996, for Precooling System for Joule-Thomson Probe, which was a continuation-in-part of prior copending U.S. patent application Ser. No. 08/698,044, filed Aug. 15, 1996, for Mixed Gas Refrigeration Method, which was a continuation-in-part of U.S. patent application Ser. No. 08/542,123, filed Oct 12, 1995, for Miniature Mixed Gas Refrigeration System. This application also claims priority from U.S. Provisional Patent Application Ser. No. 60/054,168, filed Jul. 30, 1997, for Closed Loop Cryosurgical Device. These prior applications are completely incorporated herein by reference.

STATEMENT REGARDING FEDERALLY SPONSORED RESEARCH OR DEVELOPMENT

The U.S. Government has a paid up license in this invention and the right to have this invention practiced on behalf of the Government, as provided for by the terms of Contract No. CRADA: CN-1090, awarded by the National Institute of Standards and Technology.

BACKGROUND OF THE INVENTION

1. Field of the Invention

This invention is in the field of cooling biological tissues to very low temperatures, for treatment of medical conditions, as in cryosurgery.

2. Background Information

It is desirable to be able to selectively cool miniature discrete portions of biological tissue to very low temperatures in the performance of cryosurgery, without substantially cooling adjacent tissues of the organ. Cryosurgery has become an important procedure in medical, dental, and veterinary fields. Particular success has been experienced in the specialties of gynecology and dermatology. Other specialties, such as neurosurgery and urology, could also benefit from the implementation of cryosurgical techniques, but this has only occurred in a limited way. Unfortunately, currently known cryosurgical instruments have several limitations which make their use difficult or impossible in some such fields. Specifically, known systems are not optimally designed to have sufficient precision and flexibility to allow their widespread use endoscopically and percutaneously.

In the performance of cryosurgery, it is typical to use a cryosurgical application system designed to suitably freeze the target tissue, thereby destroying diseased or degenerated cells in the tissue. The abnormal cells to be destroyed are often surrounded by healthy tissue which must be left uninjured. The particular probe, catheter, or other applicator used in a given application is therefore designed with the optimum shape, size, and flexibility or rigidity for the application, to achieve this selective freezing of tissue. Where a probe or catheter is used, the remainder of the refrigeration system must be designed to provide adequate cooling, which involves lowering the operative portion of the probe to a desired temperature, and having sufficient power or capacity to maintain the desired temperature for a given heat load. The entire system must be designed to place the operative portion of the probe or catheter at the location of the tissue to be frozen, without having any undesirable effect on other organs or systems.

Currently known cryosurgical systems typically use liquid nitrogen or nitrous oxide as coolant fluids. Liquid nitrogen is usually either sprayed onto the tissue to be destroyed, or it is circulated to cool a probe which is applied to the tissue. Liquid nitrogen has an extremely low temperature of approximately 77 K, and a high cooling power, making it very desirable for this purpose. However, in these systems, liquid nitrogen typically evaporates and escapes to the atmosphere during use, requiring the continual replacement of storage tanks. Further, since the liquid is so cold, the probes and other equipment used for its application require vacuum jackets or other types of insulation. This makes the probes relatively complex, bulky, and rigid, and therefore unsuitable for endoscopic or intravascular use. The need for relatively bulky supply hoses and the progressive cooling of all the related components make the liquid nitrogen instruments less than comfortable for the physician, as well, and they can cause undesired tissue damage.

A nitrous oxide system typically achieves cooling by pressurizing the gas and then expanding it through a Joule-Thomson expansion element, such as a valve, orifice, or other type of flow constriction, at the end of a probe tip. The typical nitrous oxide system pressurizes the gas to 700 to 800 psia., to reach practical temperatures of no lower than about 190 K to 210 K. Nitrous oxide systems are not able to approach the temperature and power achieved by the nitrogen systems. The maximum temperature drop that can be achieved in a nitrous oxide system is to 184 K, which is the boiling point of nitrous oxide. The nitrous oxide system does have some advantages, in that the inlet high pressure gas is essentially at room temperature until it reaches the Joule-Thomson element at the probe tip. This eliminates the need for insulation of the system, facilitating miniaturization and flexibility to some extent. However, because of the relatively warm temperatures and low power, tissue destruction and other applications are limited. For many such applications, temperatures below 184 K are desirable. Further, the nitrous oxide must typically be vented to atmosphere after passing through the system, since affordable compressors suitable for achieving the high pressures required are not reliable and readily commercially available.

In most Joule-Thomson systems, single non-ideal gasses are pressurized and then expanded through a throttling component or expansion element, to produce isenthalpic cooling. The characteristics of the gas used, such as boiling point, inversion temperature, critical temperature, and critical pressure determine the starting pressure needed to reach a desired cooling temperature. Joule-Thomson systems typically use a heat exchanger to cool the incoming high pressure gas with the outgoing expanded gas, to achieve a higher drop in temperature upon expansion and greater cooling power. For a given Joule-Thomson system, the desired cooling dictates the required heat exchanger capacity.

Specifically, it would be desirable to develop a refrigeration system which can apply the necessary cooling power through a long, slender, flexible catheter, such as a transvascular cardiac catheter, or a cryoprobe. Cardiac catheters must be very slender, in the range of less than 5 mm., and they must exhibit considerable flexibility, in order to be inserted from an access point in a remote blood vessel into the heart. A cryosurgical catheter to be used in such an application must also have a relatively low operating pressure for safety reasons. It must have the cooling power to overcome the ambient heat load imposed by the circulating blood, yet it must be able to achieve a sufficiently low temperature to destroy the target tissue. Finally, the cold heat transfer element must be limited to the tip or end region of the catheter, in order to prevent the damaging of tissue other than the target tissue.

It is an object of the present invention to provide a method and apparatus for precooling a primary loop high pressure refrigerant with a secondary loop refrigeration cycle which uses a different refrigerant from the primary loop, and then using the primary loop high pressure refrigerant to achieve a sufficiently low temperature, utilizing a pressure which is safe for cryosurgery, with components capable of fitting within a hand held cryoprobe or flexible intravascular catheter.

BRIEF SUMMARY OF THE INVENTION

The present invention comprises a miniature refrigeration system, including a method for operating the system, including precooling of the primary high pressure refrigerant with a secondary closed loop refrigeration cycle using a second refrigerant, to maximize the available cooling power of the first refrigerant.

The cooling power is an important design parameter of a cryosurgical instrument. With greater cooling power, more rapid temperature decreases occur, and lower temperatures can be maintained at the probe tip during freezing. This ultimately leads to greater tissue destruction. The power of a J-T cryosurgical device is a function of the enthalpy difference of the primary refrigerant and the mass flow rate. Pre-cooling certain refrigerants will increase the enthalpy difference available for cooling power. In addition, pre-cooling will increase the average mass flow rate by making the gas more dense.

Pre-cooling has two other important ramifications. First, it reduces the size of primary-to-primary heat exchangers used in the probe or catheter. In the miniature environments envisioned for the used of this apparatus, severe size limitations will be placed upon the heat exchangers used. Second, J-T cryosurgical devices require fixed size expansion elements, which can become partially or totally blocked by contaminants such as water or oil. This limits flow rate and decreases cooling power. Pre-cooling allows these contaminants to be cold-filtered and removed from circulation prior to reaching the expansion element.

The primary closed loop refrigeration system has a primary loop compressor for compressing a primary refrigerant to a pressure up to 350 psia. An example of a suitable primary refrigerant is SUVA-95 made by DuPont Fluoroproducts, Chestnut Run Plaza, Wilmington, Delaware. Primary refrigerant mixtures of three or more constituent gases may also be used, as disclosed in parent application 08/698,004. The method and apparatus of the present invention can be used equally well in a rigid hand held cryoprobe, or in a catheter.

The high pressure primary refrigerant from the primary compressor is fed into a high pressure supply tube, such as an inner tube of a coaxial dual lumen tube leading to the handle of a cryoprobe, or to the proximal end of a flexible catheter. The dual lumen tube feeds the high pressure refrigerant into the inlet port at the proximal end of a miniature primary-to-secondary heat exchanger, which can be located in the handle of the cryoprobe, or at the proximal end of a flexible catheter. The high pressure primary refrigerant passes through the high pressure passageway within the primary-to-secondary heat exchanger and exits through a port at the distal end of the primary-to-secondary heat exchanger. If required, a primary-to-primary heat exchanger can be interposed between the compressor and the primary-to-secondary heat exchanger.

The primary-to-secondary heat exchanger is part of the secondary closed loop refrigeration system which has a secondary compressor and a secondary expansion element, in addition to the primary-to-secondary heat exchanger. The secondary compressor unit compresses and condenses a secondary refrigerant, different from the primary refrigerant, to a pressure which can be relatively higher than that used in the primary loop. A suitable secondary refrigerant is a 50/50 mix of difluoromethane and pentafluoroethane, or a 50/50 mix of pentafluoroethane and 1,1,1 trifluoroethane. Since the secondary loop does not flow into the probe or catheter, a higher pressure can be used safely. After passing through the condenser, the secondary refrigerant liquid passes through the secondary expansion element, in which the secondary refrigerant liquid evaporates and expands to a lower temperature.

The low pressure secondary refrigerant then passes through a low pressure secondary passageway in the primary-to-secondary heat exchanger and returns to the secondary compressor.

The outlet of the high pressure primary passageway of the primary-to-secondary heat exchanger can be connected to the inlet of a high pressure passageway in a miniature primary-to-primary heat exchanger located in the probe handle or at the proximal end of the catheter. The high pressure primary refrigerant passes through the high pressure passageway within the miniature primary-to-primary heat exchanger and exits through a port at the distal end of the heat exchanger. The high pressure passageway is then connected to the inlet of the primary Joule-Thomson expansion element located in the cold tip, in which the primary refrigerant is expanded to a lower pressure and a lower temperature, which can be as low as 148 K. If the primary-to-secondary heat exchanger has sufficient capacity, it may not be necessary to incorporate the first primary-to-primary heat exchanger.

The primary refrigerant exiting the primary Joule-Thomson expansion element is exposed to the inner surface of a heat transfer element mounted in the wall of an outer tube which is coaxial with the inner tube. The expanded primary refrigerant cools the heat transfer element to a lower temperature and then returns through the low pressure return passageway of the miniature primary-to-primary heat exchanger. This cools the primary high pressure refrigerant from its precooled temperature to a lower temperature. From the low pressure outlet of the miniature primary-to-primary heat exchanger, the low pressure expanded primary refrigerant flows to the first primary-to-primary heat exchanger, if present, or directly into the lumen of the outer coaxial tube, outside the inner high pressure tube, to return to the primary compressor.

Both the primary-to-secondary heat exchanger and the primary-to-primary heat exchanger can be coiled tube heat exchangers or finned tube heat exchangers. The primary-to-primary heat exchanger can be a coiled coaxial tube, with the inner lumen being the high pressure passageway and the outer lumen being the low pressure passageway. The secondary passageways of the primary-to-secondary heat exchanger can be a coiled coaxial tube, with the outer lumen being the low pressure secondary passageway. Attached to the side of this outer tube, in a parallel arrangement, is a tube which forms the high pressure primary passageway. The high pressure primary tube can have a plurality of inner tubes, which can be nested and placed in contact with the outer tube for improved heat exchange. High pressure primary refrigerant flows in all of the nested tubes and in the interstitial spaces between the nested tubes and the outer tube. The secondary tube and the primary tube can be formed of metal and soldered together.

Alternatively, the primary-to-secondary heat exchanger can consist of a coiled finned tube for the primary refrigerant, within a can into which the secondary refrigerant is expanded.

The miniature primary-to-primary heat exchanger can be a single coiled finned tube surrounded by a low pressure return passageway.

The primary Joule-Thomson expansion element can be a sintered metal plug made by sintering a plurality of metal beads into a metal cup, to provide the required pressure drop. Alternatively, the expansion element can be a properly sized orifice or some other type of restriction. The two different stages of the sintered plug expansion element, if present, can utilize different sizes of beads, different cross sectional areas, and different packing densities. The heat transfer element can take the optimum shape for matching the object or tissue to be cooled. For example, a metal plug can be installed in the tip of the outer tube or catheter, for applying cooling through the extreme distal tip of the catheter. Alternatively, a relatively narrow metal strip can be mounted in a side wall of the catheter, near the distal tip, for applying cooling to a narrow strip of tissue.

The novel features of this invention, as well as the invention itself, will be best understood from the attached drawings, taken along with the following description, in which similar reference characters refer to similar parts, and in which:

DETAILED DESCRIPTION OF THE INVENTION

The present invention lies in the appropriate use of a secondary closed loop evaporative refrigeration system to precool the primary high pressure refrigerant, before passage of the primary refrigerant through the primary Joule-Thomson expansion element. This is intended to maximize the available cooling power at the tip of the cryosurgical probe or catheter.

Pre-cooling the primary refrigerant prior to feeding it to the miniature primary-to-primary heat exchanger is the focus of the present invention. This pre-cooling could be done prior to introducing the primary refrigerant into the catheter, by the use of a conventional, relatively large, heat exchanger. However, for ease of handling and for maximum efficiency, the present invention focuses on the provision of pre-cooling near the treatment area, such as in the handle of a cryoprobe, or at the proximal end of a catheter. This is because minimizing the length of the flow path of precooled refrigerant maximizes the efficiency of the pre-cooling system.

An important parameter in the design of a cryosurgical device is the cooling power which the refrigeration system can develop. The cooling power determines the rate of cooling in degrees per second, and the temperature which can be maintained at the probe tip during freezing of the tissue. The rate of freezing is important in achieving cell death, since more rapid freezing results in better formation of intracellular ice crystals, resulting in cell lysis. The rate of freezing also determines the length of time required to perform a given procedure on the patient. The quicker the procedure, the less traumatic the procedure is to the patient.

The temperature which can be maintained at the probe cold tip determines the size of the ice ball formed in the surrounding tissue. This, of course, determines the total volume of tissue destroyed at each location, and the speed with which the procedure can be completed. For example, if a first cryoprobe, using a given refrigerant, has 30 watts of cooling power, assume that it can maintain a cold tip temperature of minus 100 degrees C., creating an ice ball of up to 4.5 cm diameter in 15 minutes, in a test gel. Because of the rapid temperature drop, a significant percentage of cell death would occur within a similar size ball of living tissue. By contrast, consider a second cryoprobe, using the same refrigerant, which has only 10 watts of cooling power. The second cryoprobe could only maintain a temperature of minus 50 degrees C., creating an ice ball only 2.5 cm diameter within 15 minutes. Therefore, the aforementioned high percentage of cell death would only occur in a 2.5 cm diameter ball of living tissue, rather than a 4.5 cm diameter ball. Furthermore, if the required size of the ice ball is only 2.5 cm, the first cryoprobe could achieve such an ice ball within 5 minutes, rather than 15 minutes. So, by either standard, the first cryoprobe will achieve a better result, and more quickly, than the lower power second cryoprobe.

In Joule-Thomson cryosurgical devices, high pressure fluid expands across a restriction of some kind, such as a small orifice, or a crimped tube. The sudden drop in pressure results in a corresponding drop in temperature. The cooling power of the device is the product of the mass flow rate of the cryogen and the enthalpy difference at the different pressures and temperatures. The flow rate is a function of orifice size and the temperature and pressure of the cryogen. For a given orifice size, under non-choking conditions, the density of the cryogen is higher at higher pressures and lower temperatures, resulting in a higher mass flow rate. The maximum flow rate is found at the point where the cryogen is a liquid. The enthalpy difference is also a function of the pressure and temperature, with the enthalpy difference between two conditions being higher at higher pressures and lower temperatures. For a given temperature and a given pressure, the maximum enthalpy difference between two conditions occurs at the liquefaction point of the cryogen. Incorporating one or more pre-cooling heat exchangers into the refrigeration system promotes cooling or liquefaction of the warm, high pressure cryogen, thereby increasing the power of the system.

Nitrous oxide is the most commonly used cryogen in Joule-Thomson cryosurgical systems. If the high pressure of the system is above 4.5 MPa, nitrous oxide will liquefy upon expansion, without the help of a heat exchanger, and achieve the maximum cooling power. However, nitrous oxide must be operated at this high pressure, and the lowest temperatures available are between minus 50 and minus 70 degrees C., which is relatively warm for some cryosurgical applications. Therefore, the safety and the efficiency of a nitrous oxide system are less than desirable for some applications, such as catheter ablation of heart tissue, and ablation of endometrial tissue.

The refrigerants discussed in this application operate at lower pressures, and they can achieve lower temperatures, making them both safer and more effective. However, these refrigerants will not reach their maximum cooling power, without the aid of a heat exchanger.

This creates a problem, if this type of refrigerant is to be used. Since the refrigerant is in the warm, gaseous state upon startup of the refrigeration system, the early flow rate is very low, and the power is very low. If the heat exchanger used is not very efficient, the initial cool down is very slow at overcoming the low flow rate. Further, the cold tip is typically placed within the patient, and in contact with the target tissue, before commencement of cooldown, placing a significant heat load on the tip. This means that cooldown can be unacceptably slow, and in some cases, it may not occur at all.

Another problem that may occur is the clogging of the expansion element by contaminants. If present, water and oil will liquefy and freeze as the temperature of the cryogen drops. Because of the small size of the orifice or other expansion element, it can be plugged easily. In larger cryosystems, an adjustable orifice can be used, to offset this clogging. However, in the small medical systems, adjustable orifices are too large and unwieldy to be used.

In order to maximize the performance of the present cryosurgical system, and to eliminate the problems normally associated with slow cooldown rates and low cooling power, an independent closed loop secondary evaporative refrigeration system is incorporated. The secondary system uses a refrigerant such as a 50/50 mix of difluoromethane and pentafluoroethane, or a 50/50 mix of pentafluoroethane and 1,1,1 trifluoroethane, to pre-cool the primary refrigerant in the handle of the cryoprobe or at the proximal end of the catheter, prior to flow of the primary refrigerant to the cold tip. The secondary system accomplishes this pre-cooling through a primary-to-secondary heat exchanger placed as close as possible to the cold tip, to prevent excessive warming of the cooled primary refrigerant before it reaches the cold tip.

This pre-cooling causes the initial flow rate and the cooling power of the system to be higher, making the initial cooldown rate much faster. With some refrigerants, and with pre-cooling, there may be no need for a heat exchanger at the cold tip next to the primary expansion element. A further advantage is that the pre-cooler may act as a cold filter, to eliminate contaminants such as oil and water, which may otherwise clog the expansion element as the system cools down.

The size and inherent heat transfer capacity of the primary-to-primary heat exchanger are limited, regardless of the design used. This suggests that the overall refrigeration system be kept at the highest possible level of performance by the use of a secondary closed loop refrigeration system. When appropriate precooling is combined with the optimum refrigerant, the system will perform cooling as well as possible, in spite of the size limitations. The goal of this precooling system is to maximize the cooling power of the combination of the heat exchangers and the expansion elements.

Figure 1:
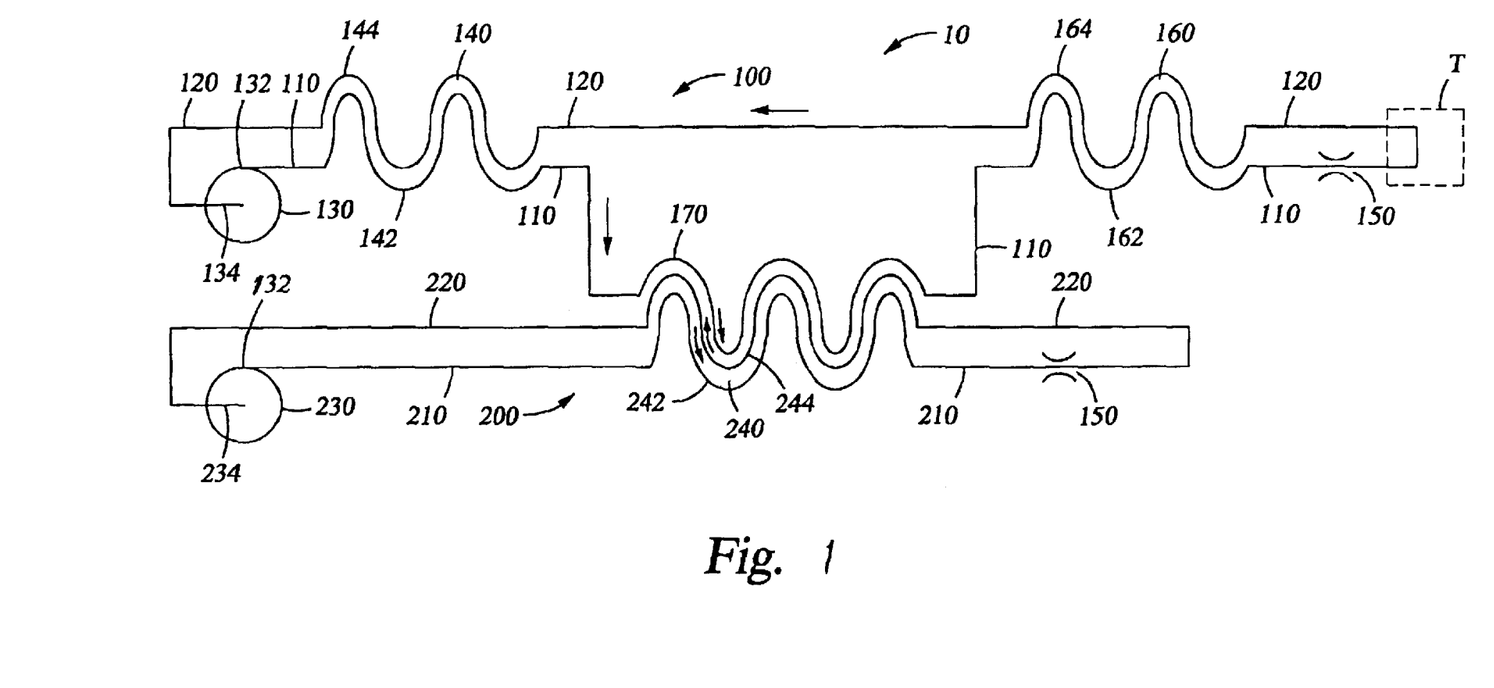
FIG. 1 is a schematic of the primary and secondary closed loops of the present invention.

FIG. 1 shows a schematic of the dual closed loop refrigeration system 10 of the present invention, incorporating the precooling concept. The primary loop 100 consists of a high pressure path 110 and a low pressure path 120. A primary loop compressor 130 compresses the primary refrigerant to a selected pressure and temperature. The high pressure primary refrigerant, such as SUVA-95, then flows from the outlet 132 of the primary compressor 130, through an optional first primary-to-primary heat exchanger 140, which can be a miniature heat exchanger located in the handle of a cryoprobe. Specifically, the high pressure primary refrigerant passes through the high pressure passageway 142 of the first primary-to-primary heat exchanger 140, where it is cooled to a lower temperature. Depending upon the reqired temperatures and cooling power, some applications may not require the first primary-to-primary heat exchanger 140.

The high pressure primary refrigerant then passes through a primary-to-secondary heat exchanger 240, specifically through the high pressure primary passageway 170 of the primary-to-secondary heat exchanger 240, where it is further cooled to a lower temperature. The high pressure primary refrigerant then passes through a second primary-to-primary heat exchanger 160, specifically through the high pressure passageway 162, where it is still further cooled. This second primary-to-primary heat exchanger 160 can be located in the distal tip of a cryoprobe or catheter, or it can be located in the handle of the cryoprobe or at the proximal end of the catheter.

The high pressure primary refrigerant then flows to the primary Joule-Thomson expansion element 150. After expansion in the primary expansion element 150, to a final temperature such as 148 K, the expanded low pressure refrigerant cools the target tissue T.

Then, the low pressure primary refrigerant passes back through a low pressure passageway 164 in the second primary-to-primary heat exchanger 160, where it is warmed, and through a low pressure passageway 144 in the first primary-to-primary heat exchanger 140, where it is further warmed. The low pressure primary refrigerant then returns to the inlet 134 of the primary compressor 130.

The secondary loop 200 consists of a high pressure path 210 and a low pressure path 220. A secondary loop compressor unit 230 compresses and condenses the secondary refrigerant, such as a 50/50 mix of difluoromethane and pentafluoroethane, or a 50/50 mix of pentafluoroethane and 1,1,1 trifluoroethane, at a pressure which can be relatively higher than the pressure found in the primary system, since the secondary system does not enter the cannula of the probe, or the catheter. The high pressure secondary refrigerant liquid then can flow from the outlet 232 of the secondary compressor unit 230, either through or bypassing a primary-to-secondary heat exchanger 240, which can also be a miniature heat exchanger located in the handle of the cryoprobe. If the high pressure secondary refrigerant liquid passes through a secondary high pressure passageway 242 of the primary-to-secondary heat exchanger 240, it is cooled to a lower temperature.

The high pressure secondary refrigerant then passes through a secondary expansion element 250. After vaporization and expansion in the secondary expansion element 250, the expanded low pressure secondary refrigerant gas passes through a low pressure passageway 244 in the primary-to-secondary heat exchanger 240. The low pressure secondary refrigerant then returns to the inlet 234 of the secondary compressor unit 230.

Figure 2:
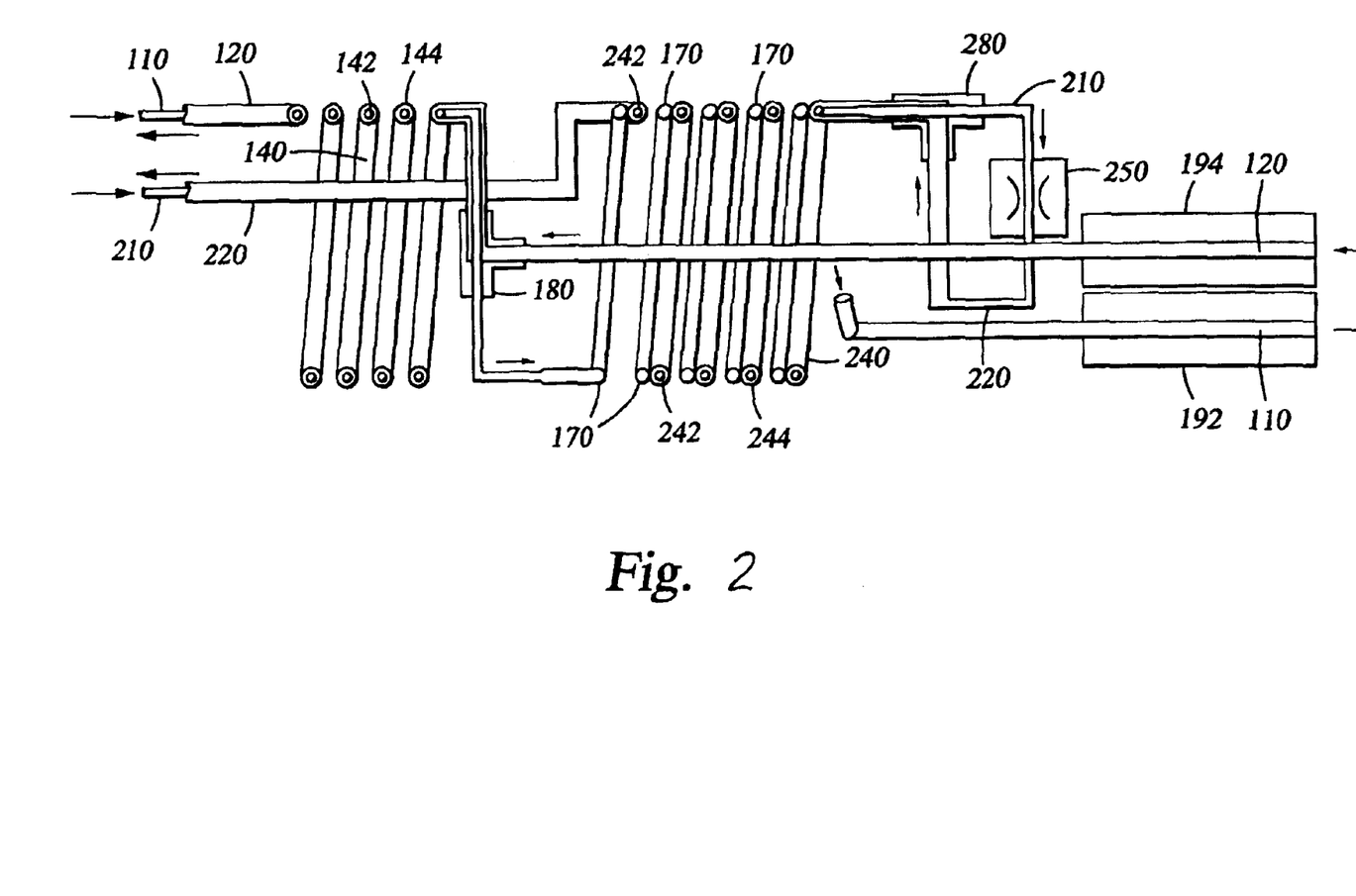
FIG. 2 is a section view of one embodiment of a portion of the primary closed loop and the secondary closed loop of the present invention, with coaxial tube heat exchangers, as they could be arranged in the handle of a cryoprobe.
Figure 4:
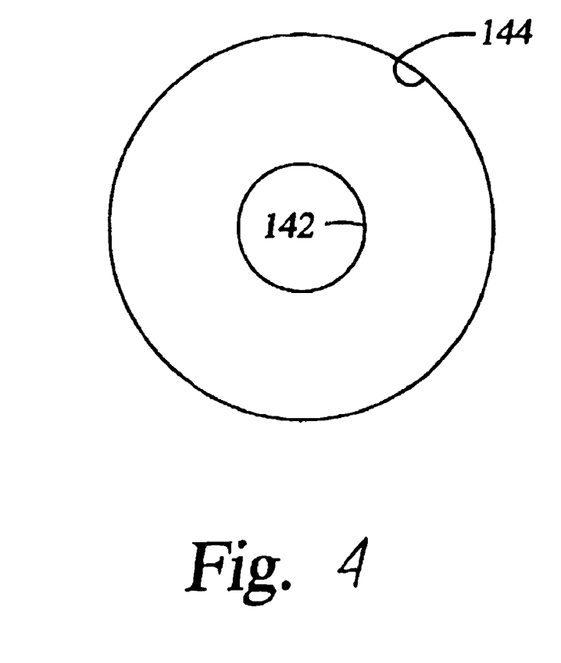
FIG. 4 is a transverse section view of the coaxial dual lumen tube used in the first primary-to-primary heat exchanger shown in FIG. 2.

FIG. 2 shows a first embodiment of the portion of the dual loop refrigeration system that might be located in the handle of a cryoprobe, or at the proximal end of a catheter. The primary loop 100 enters the handle as a coaxial dual lumen tube, with the high pressure path 110 being in the inner lumen, and the low pressure path 120 being in the outer lumen. The first primary-to-primary heat exchanger 140 in this embodiment is constructed as a coaxial coiled tube, with the high pressure passageway 142 being in the inner lumen, and the low pressure passageway 144 being in the outer lumen. The details of the dual lumen coaxial tube are shown in FIG. 4. Both the high and low pressure paths 110, 120 pass into a first splitting tee fitting 180. In the splitting tee fitting 180, the high pressure path 110 is split from the low pressure path 120. From the first tee fitting 180, the high pressure path 110 passes to the high pressure primary passageway 170 in the primary-to-secondary heat exchanger 240.

Figure 5:
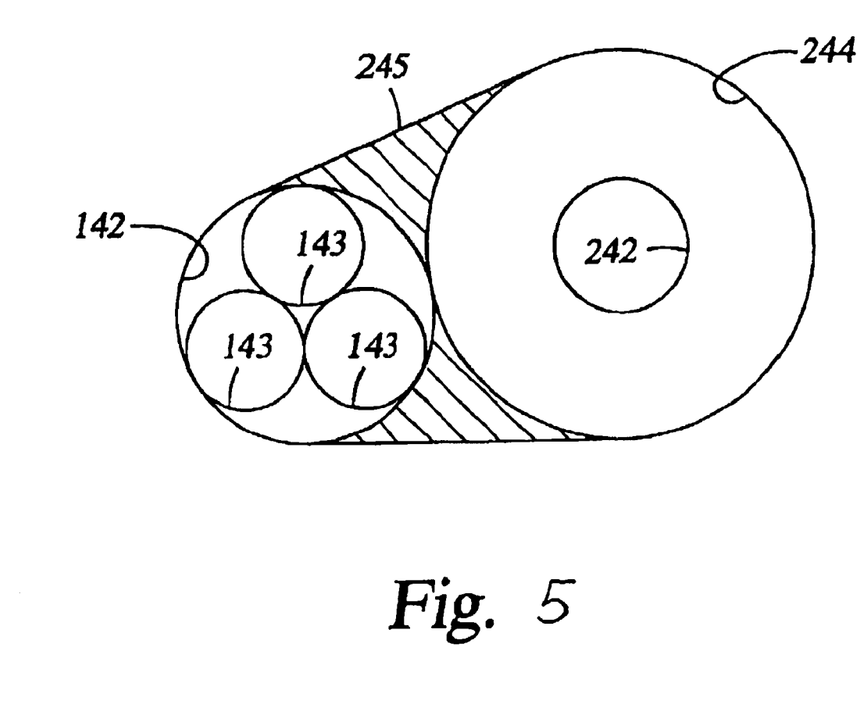
FIG. 5 is a transverse section view of the multiple lumen tubes used in the primary-to-secondary heat exchanger shown in FIG. 2.

The primary-to-secondary heat exchanger 240 in this embodiment is constructed as a coiled multi-lumen tube, as shown in FIG. 5. The high and low pressure secondary paths 210, 220 can pass through a dual lumen coaxial tube, or the high pressure secondary path 210 can bypass the primary-to-secondary heat exchanger 240. If the high pressure secondary path 210 passes through the primary-to-secondary heat exchanger 240, it passes through the inner lumen, high pressure secondary passageway 242, and the low pressure secondary path 220 passes through the outer lumen, low pressure secondary passageway 244. Whether or not the high pressure secondary path 210 goes through the primary-to-secondary heat exchanger 240, the high pressure primary passageway 142 is soldered to the outside of the low pressure secondary passageway 244. The high pressure primary passageway 142 can have a plurality of inner lumens 143, with the high pressure primary refrigerant flowing through all of the inner lumens 143, and through the interstitial spaces between and around the inner lumens 143. This arrangement promotes improved heat transfer to the solder and to the low pressure secondary passageway 244.

After exiting the primary-to-secondary heat exchanger 240, the high pressure primary path 110 flows through a high pressure primary connector 192, which can be connected to the cannula of the cryoprobe or the proximal end of a flexible catheter, and to the primary expansion element 150 in the cold tip. After expansion in the expansion element 150, the low pressure gas mixture flows back through a low pressure primary connector 194 to the tee fitting 180. In the tee fitting 180, the low pressure primary passageway 144 rejoins the high pressure primary passageway 142 in a coaxial relationship to return to the primary compressor 130.

The secondary loop 200 also enters the cryoprobe handle, coming from the secondary compressor unit 230, as a coaxial dual lumen tube, with the high pressure path 210 being in the inner lumen, and the low pressure path 220 being in the outer lumen. The secondary high and low pressure paths 210, 220 pass through the primary-to-secondary heat exchanger 240 as described above, and connect to a second splitting tee fitting 280. In the second tee fitting 280, the high pressure secondary path 210 splits from the low pressure secondary path 220 and passes through the secondary expansion element 250. After expansion in the secondary expansion element 250, the low pressure secondary refrigerant passes into the low pressure secondary path 220, which rejoins the high pressure secondary path 210 in the second tee fitting 280. Alternatively, the secondary high pressure path 210 can bypass the primary-to-secondary heat exchanger 240, go directly through the secondary expansion element 250, and the low pressure secondary path 220 can then pass back through the primary-to-secondary heat exchanger 240.

Figure 3:
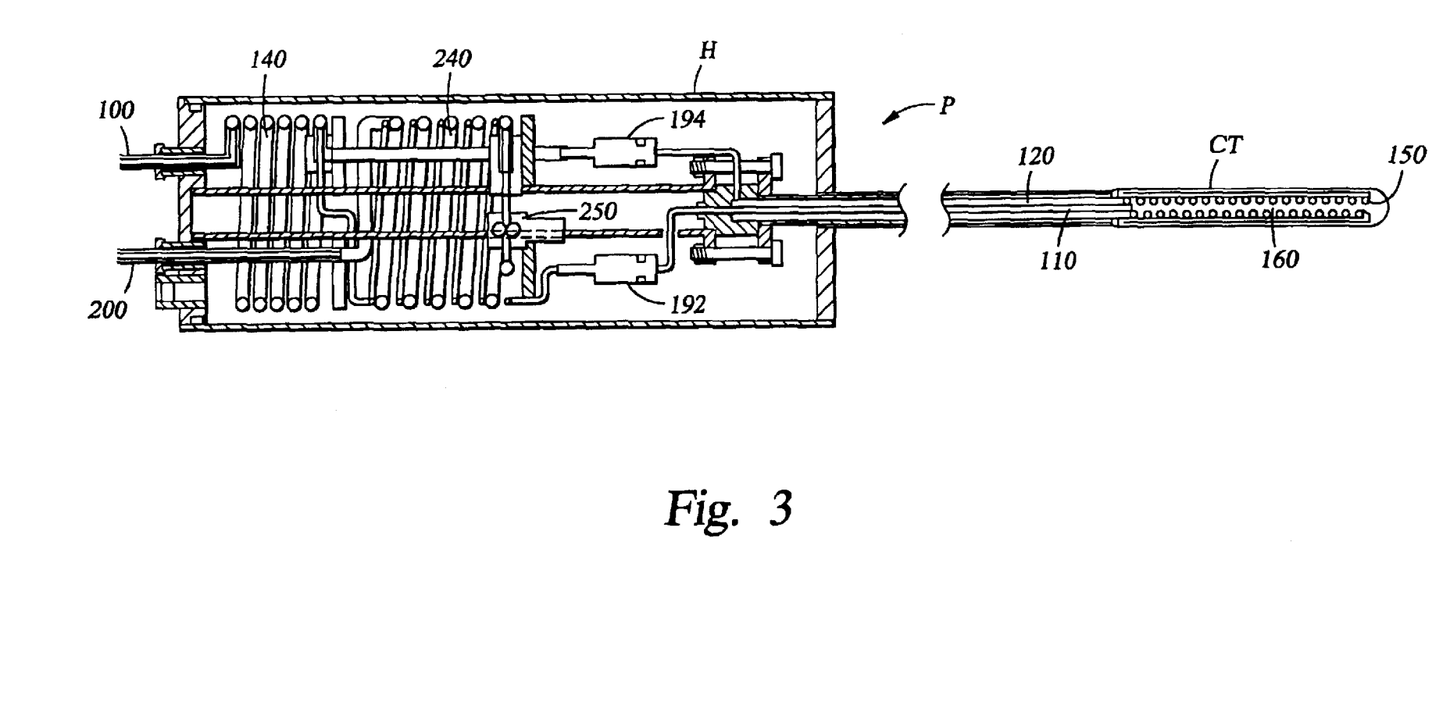
FIG. 3 is a section view of a hand held cryoprobe incorporating the embodiment of the present invention shown in FIG. 2.

FIG. 3 shows how the first embodiment of the present invention might be arranged in a rigid cryoprobe P, having a handle H. The primary and secondary closed loop systems 100, 200 enter the end of the handle H. The primary refrigerant passes through the first primary-to-primary heat exchanger 140, while the first primary-to-primary heat exchanger 140 is bypassed by the secondary refrigerant. Both the primary high pressure refrigerant and the secondary low pressure refrigerant pass through the primary-to-secondary heat exchanger 240 as described earlier. The secondary refrigerant is vaporized and expanded in the secondary expansion element 250 and returns through the primary-to-secondary heat exchanger 240. The low pressure secondary refrigerant then exits the handle H to return to the secondary compressor unit 230. The primary refrigerant passes through the connectors 192, 194 to the cold tip CT. In this embodiment, in the cold tip CT, the high pressure primary refrigerant passes through the primary-to-primary heat exchanger 160, and then through the primary expansion element 150. The primary-to-primary heat exchanger 160 can be a coiled high pressure tube, with the low pressure primary refrigerant returning through the coils. Having expanded and cooled, the low pressure primary refrigerant flows back through the second primary-to-primary heat exchanger 160, and the first primary-to-primary heat exchanger 140, if present, before exiting the handle H to return to the primary compressor 130.

Figure 6:
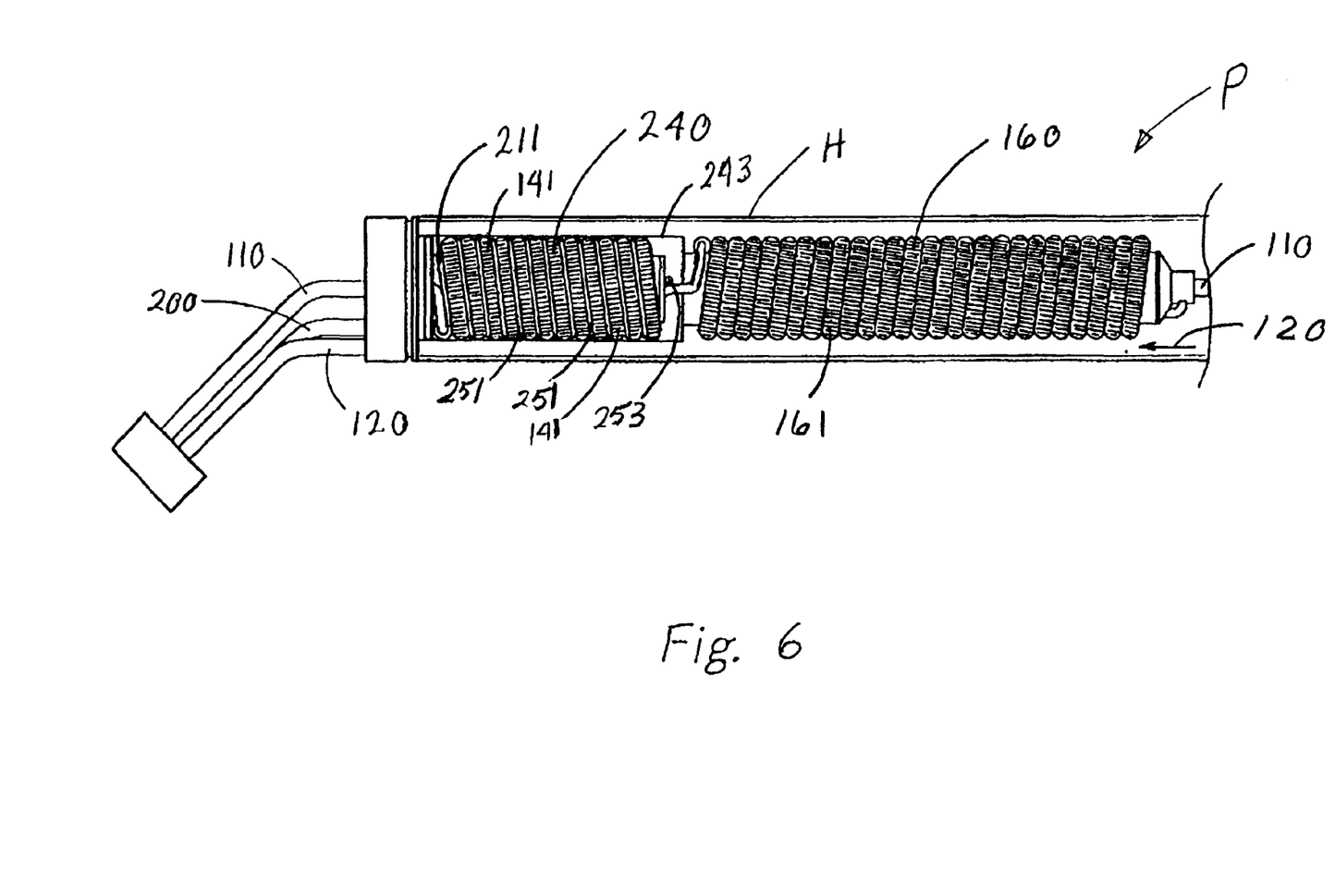
FIG. 6 is a partial longitudinal section of a second embodiment of the present invention, with finned tube heat exchangers.

FIG. 6 shows how a second embodiment of the present invention might be arranged in a rigid cryoprobe P, having a handle H. The handle H can be formed as a vacuum jacketed dewar. The primary and secondary closed loop systems 100, 200 enter the end of the handle H. In this embodiment, the high pressure primary path 110 and the low pressure primary path 120 are not coaxial. The high pressure primary refrigerant passes through a finned tube 141, which is coiled within a can 243 encompassing the primary-to-secondary heat exchanger 240. The high pressure primary refrigerant then exits the primary-to-secondary heat exchanger 240 and enters the primary-to-primary heat exchanger 160, which in this embodiment is located in the cryoprobe handle H.

The secondary refrigerant is vaporized and expanded in a capillary tube 251, which comprises the secondary expansion element. The capillary tube 251 is coiled around the outer periphery of the high pressure primary finned tube 141, in the helical groove formed by the outer edges of the fins. After exiting the outlet 253 of the capillary tube 251, the low pressure secondary refrigerant passes between the fins of the finned tube 141 as it returns through the primary-to-secondary heat exchanger 240. The low pressure secondary refrigerant then exits the handle H to return to the secondary compressor unit 230.

The primary refrigerant passes through a second high pressure primary finned tube 161 in the primary-to-primary heat exchanger 160, and then through the primary expansion element 150. Having expanded and cooled, the low pressure primary refrigerant flows back through the primary-to-primary heat exchanger 160, passing between the fins, before exiting the handle H to return to the primary compressor 130.

While the particular invention as herein shown and disclosed in detail is fully capable of fulfilling the objects previously stated, it is to be understood that this disclosure is merely an illustration of the presently preferred embodiments of the invention and that no limitations are intended other than those described in the appended claims.

We claim:

1. A dual stage cryosurgical device, comprising:
   a primary compressor for compressing a primary refrigerant in a primary loop;
   a secondary compressor for compressing a secondary refrigerant in a secondary loop separate from said primary loop, said secondary refrigerant being compressed to a higher pressure than said primary refrigerant, said secondary refrigerant being different from said primary refrigerant;
   a secondary expansion element for expanding said secondary refrigerant;
   a primary-to-secondary heat exchanger for cooling said primary refrigerant with said expanded secondary refrigerant;
   a conduit for conducting said primary refrigerant from said primary-to-secondary heat exchanger to a selected cryosurgical target tissue;
   a cold tip on a distal end of said conduit; and
   a primary expansion element in said cold tip for expanding said primary refrigerant, said cold tip being cooled by said expanded primary refrigerant, for applying cooling to said cryosurgical target tissue.

2. A dual stage cryosurgical device as recited in claim 1, further comprising a primary-to-primary heat exchanger for cooling said compressed primary refrigerant with said expanded primary refrigerant.

3. A dual stage cryosurgical device as recited in claim 2, wherein said primary-to-primary heat exchanger is between said primary compressor and said primary-to-secondary heat exchanger.

4. A dual stage cryosurgical device as recited in claim 2, wherein said primary-to-primary heat exchanger is between said primary-to-secondary heat exchanger and said primary expansion element.

5. A miniature cryosurgical system, comprising:
   a closed primary loop for circulating a primary refrigerant, with a high pressure primary flow path and a low pressure primary flow path, said primary loop including a primary compressor, and a primary expansion element for expanding said primary refrigerant from a high pressure gaseous state in said high pressure primary flow path to a low pressure gaseous state in said low pressure primary flow path; and
   a closed secondary loop for circulating a secondary refrigerant, with a high pressure secondary flow path and a low pressure secondary flow path, said secondary loop including a secondary compressor, a condenser, a primary-to-secondary heat exchanger, and a secondary expansion element within said primary-to-secondary heat exchanger for vaporizing and expanding said secondary refrigerant from a liquid state in said high pressure secondary flow path to a gaseous state in said low pressure secondary flow path;
   wherein said high pressure primary refrigerant and said low pressure secondary refrigerant pass through said primary-to-secondary heat exchanger in a heat exchange relationship; and
   wherein said low pressure primary refrigerant bypasses said primary-to-secondary heat exchanger.

6. A miniature cryosurgical system as recited in claim 5, further comprising a primary-to-primary heat exchanger, having high pressure and low pressure primary flow paths.

7. A miniature cryosurgical system as recited in claim 6, wherein said primary-to-primary heat exchanger is between said primary compressor and said primary-to-secondary heat exchanger.

8. A miniature cryosurgical system as recited in claim 6, wherein said primary-to-primary heat exchanger is between said primary-to-secondary heat exchanger and said primary expansion element.

9. A miniature cryosurgical system as recited in claim 6, wherein said primary-to-primary heat exchanger comprises a coaxial dual lumen coiled tube, with said high pressure primary flow path connected to an inner said lumen and said low pressure primary flow path connected to an outer said lumen.

10. A miniature cryosurgical system as recited in claim 6, wherein said primary-to-primary heat exchanger comprises a coiled finned tube, with said high pressure primary flow path in an inner lumen and said low pressure primary flow path between fins of said finned tube.

11. A miniature cryosurgical system as recited in claim 5, wherein said primary-to-secondary heat exchanger comprises a coiled finned tube, with said high pressure primary flow path in an inner lumen and said low pressure secondary flow path between fins of said finned tube.

12. A miniature cryosurgical system as recited in claim 5, wherein said primary-to-secondary heat exchanger comprises a multi-lumen coiled tube, with said high pressure primary flow path in at least one lumen of said multi-lumen tube, and said low pressure secondary flow path in at least one lumen of said multi-lumen tube.

13. A miniature cryosurgical system as recited in claim 5, wherein said primary-to-secondary heat exchanger is located proximal to said primary expansion element.

14. A miniature cryosurgical system as recited in claim 5, wherein said secondary loop is separate from said primary loop.

15. A method for performing cryosurgery on selected tissue, comprising:
   providing a closed primary loop, said primary loop including at least one primary-to-primary heat exchanger and a primary expansion element distal of said primary-to-primary heat exchanger;
   providing a closed secondary loop, said secondary loop including a primary-to-secondary heat exchanger and a secondary expansion element within said primary-to-secondary heat exchanger;
   compressing a secondary refrigerant in said secondary loop;
   vaporizing and expanding said secondary refrigerant to a lower temperature within said primary-to-secondary heat exchanger, with said secondary expansion element;
   adding enthalpy to said expanded secondary refrigerant in said primary-to-secondary heat exchanger;
   compressing a primary refrigerant, different from said secondary refrigerant, in said primary loop;
   removing enthalpy from said compressed primary refrigerant in said primary-to-secondary heat exchanger;
   removing enthalpy from said compressed primary refrigerant in said primary-to-primary heat exchanger;
   expanding said primary refrigerant with said primary expansion element to still further remove enthalpy from said primary refrigerant;
   applying said expanded primary refrigerant to a cold tip of a cryosurgical probe, to lower the temperature of said cold tip; and
   applying said cold tip to the selected tissue.

16. A method as recited in claim 13, wherein said at least one primary-to-primary heat exchanger is distal to said primary-to-secondary heat exchanger, said method further comprising:

providing a proximal primary-to-primary heat exchanger;

removing enthalpy from said compressed primary refrigerant in a high pressure side of said proximal primary-to-primary heat exchanger; and adding enthalpy to said expanded primary refrigerant in a low pressure side of said proximal primary-to-primary heat exchanger after passage of said expanded primary refrigerant through a low pressure side of said distal primary-to-primary heat exchanger.

17. A method for performing cryosurgery, as recited in claim 15, wherein said primary refrigerant contains a mixture of at least three constituent gases.

18. A method for performing cryosurgery, as recited in claim 15, wherein:

said secondary loop is separate from said primary loop;

said secondary refrigerant is compressed in said separate secondary loop; and said primary refrigerant is compressed in said separate primary loop.

19. A method for cooling a cold tip of a cryosurgical probe, comprising:

providing a closed primary loop having a compressor, at least one primary-to-primary heat exchanger, and a primary expansion element adjacent to a heat transfer element in said cold tip;

providing a closed secondary loop having a compressor unit and a primary-to-secondary heat exchanger;

compressing and condensing a secondary refrigerant in said secondary loop;

vaporizing and expanding said secondary refrigerant in a low pressure secondary section of said primary-to-secondary heat exchanger;

compressing a primary refrigerant, different from said secondary refrigerant, to a selected pressure pressure lower than said secondary refrigerant;

removing enthalpy from said compressed primary refrigerant in said high pressure primary section of said primary-to-secondary heat exchanger;

expanding said primary refrigerant in said primary expansion element to further cool said primary refrigerant to a selected temperature; and absorbing heat from said heat transfer element by contact with said expanded primary refrigerant, to cool said heat transfer element to a selected temperature.

20. A method as recited in claim 19, wherein said at least one primary-to-primary heat exchanger is distal to said primary-to-secondary heat exchanger, said method further comprising:

providing a proximal primary-to-primary heat exchanger between said primary-to-secondary heat exchanger and said primary compressor;

removing enthalpy from said compressed primary refrigerant in a high pressure side of said proximal primary-to-primary heat exchanger; and adding enthalpy to said expanded primary refrigerant in a low pressure side of said proximal primary-to-primary heat exchanger after passage of said expanded primary refrigerant through a low pressure side of said distal primary-to-primary heat exchanger.

21. A method for cooling a cold tip of a cryosurgical probe, as recited in claim 19, wherein:

said secondary loop is separate from said primary loop;

said secondary refrigerant is compressed in said separate secondary loop; and said primary refrigerant is compressed in said separate primary loop.

* * * * *